United States Patent [19]

Eckstein et al.

[11] 4,145,531

[45] Mar. 20, 1979

[54] PROCESS FOR PRODUCING 2'-SUBSTITUTED-D-RIBOFURANOSYL PURINE COMPOUNDS

[75] Inventors: Fritz Eckstein; John Hobbs, both of Göttingen, Fed. Rep. of Germany

[73] Assignee: Max-Planck-Gesellschaft zur Forderung der Wissenschaften E.V., Göttingen, Fed. Rep. of Germany

[21] Appl. No.: 792,077

[22] Filed: Apr. 28, 1977

[30] Foreign Application Priority Data

Jun. 23, 1976 [DE] Fed. Rep. of Germany ....... 2628202

[51] Int. Cl.² .............................................. C07H 19/06
[52] U.S. Cl. ........................................ 536/26; 536/24; 536/23; 536/27; 536/28; 536/29
[58] Field of Search .......................... 536/24, 29, 4, 26

[56] References Cited

U.S. PATENT DOCUMENTS

| 3,419,544 | 12/1968 | Witzel et al. ............................... 536/4 |
| 3,755,295 | 8/1973 | Veheyden et al. ....................... 536/23 |
| 3,870,700 | 5/1973 | Kotick et al. ............................ 536/23 |
| 3,987,030 | 10/1976 | Suzuki et al. ............................ 536/24 |

*Primary Examiner*—Johnnie R. Brown
*Assistant Examiner*—Blondel Hazel
*Attorney, Agent, or Firm*—Sprung, Felfe, Horn, Lynch & Kramer

[57] ABSTRACT

2'-Substituted-D-ribofuranosyl purine compounds, especially 2'-azido-D-ribofuranosyl purine compounds, of the formula

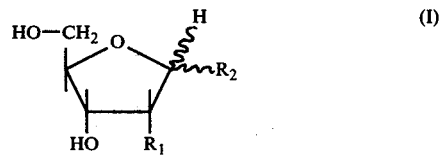

in which
  $R_1$ is azide, amino, halogen or alkoxy, and
  $R_2$ is the residue of a purine base and particularly a 9-adenyl group, a 7-guanyl group, or a 9-guanyl group (the waved lines in formula I above show that $R_2$ can be bound in the $\alpha$- or $\beta$-configuration), are prepared by a process comprising
  (a) reacting a uridine derivative with an alkali azide (when $R_1$ is to be azide or, through further conversion, an amine group) or a halide (when $R_1$ is halogen) or with an alkylating agent (when $R_1$ is alkoxy);
  (b) transforming the resulting compound with hydrazine into the corresponding 2-deoxy-ribose;
  (c) converting the 2-deoxy-ribose into a 1-O-methyl-glucoside with methanol in the presence of a strong acid;
  (d) reacting the glucoside with acetic anhydride in a polar organic solvent to form a 1-O-methyl-ribose-3,5-diacetate;
  (e) converting the diacetate with acetic anhydride in glacial acetic acid, in the presence of a strong acid into a ribose-1,3,5-triacetate;
  (f) condensing the triacetate obtained with a purine base with a purine base in which any free primary amino group is protected by acylation in an organic solvent in the presence of a Lewis acid to form (after splitting the protective acyl group) the desired compound wherein $R_1$ is azide, halogen or alkoxy;
  (g) optionally separating the product obtained into $\alpha$ and $\beta$ anomers; and
  (h) optionally reacting the said compound obtained in step (f), in which $R_1$ is azido, with triphenylphosphine in saturated methanolic ammonia to yield the corresponding compound where $R_1$ is amino.

11 Claims, No Drawings

PROCESS FOR PRODUCING 2'-SUBSTITUTED-D-RIBOFURANOSYL PURINE COMPOUNDS

This invention relates to a process for producing 2'-substituted-D-ribofuranosyl purine compounds, especially 2'-azido-D-ribofuranosyl purine compounds. In addition, the invention is directed to the novel intermediate products obtained in this process.

2'-Substituted-D-ribofuranosyl purine derivatives are valuable chemical compounds, which, on the one hand, may be used directly as chemotherapeutants since they block DNA synthesis and cause retardation of cell growth, making them particularly suitable for the treatment of tumors and cancer. On the other hand, these compounds represent valuable intermediate products for producing corresponding 5'-phosphates, -diphosphates and -triphosphates, which, themselves, effect the inhibition of certain enzymes such as $E.$ $coli$ ribonucleotide reductase; the latter in turn causes inhibition of the DNA synthesis and cell growth. Hence, these products are useful for the treatment of cancer and virus infections.

A process for converting adenosine to 2'- and 3'-azido, -amino and chlorine substituted deoxyadenosines has previously been disclosed by R. Mengel and H. Wiedner (Chem. Ber. 109 (1976), pages 433–443). The total yield attainable using this method to produce 9-(2'-azido-2'-deoxy-β-D-ribofuranosyl)-adenine is a mere 0.35%. A process for producing 9-(2'-amino-2'-deoxy-α-(and β)-D-ribofuranosyl)-adenine is known from M. L. Wolfrom and M. W. Winkley (J. Org. Chem. 32 (1967), pages 1823–1825); this synthesis proceeds from 2-glucosamine through nine stages and fourteen separate processes, providing the above compounds in yields of 1.7 and 1.6%.

There has thus been a need to produce this group of compounds, including novel compounds of a type similar to that of previously known 2'-substituted-D-ribofuranosyl purine derivatives, using a process which results in greater yields.

Surprisingly, it has been found that it is possible to convert a 2'-substituted-uridine into the corresponding 2-substituted-ribose directly by reacting the uridine with hydrazine and benzaldehyde. The riboside is an ideal starting material for producing the 2'-substituted-D-ribofuranosyl-purine derivatives.

The invention thus provides a process for producing 2'-substituted-D-ribofuranosyl-purine derivatives of the formula

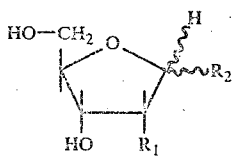

in which
R$_1$ is azide, amino, halogen or alkoxy, and
R$_2$ is the residue of a purine base and particularly a 9-adenyl group, a 7-guanyl group, or a 9-guanyl group (the waved lines in formula I above show that R$_2$ can be bound in the α- or β-configuration), which process comprises
(a) converting a uridine of the formula

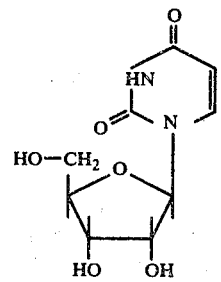

into the corresponding R$_1$' substituted compound III below, by reacting the derived O$^2$,2'-cyclo uridine with an alkali azide (when R$_1$' is azide) or with a halide (when R$_1$', is halogen), or the uridine with an alkylation agent (when R$_1$' is alkoxy)

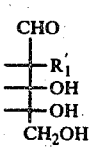

wherein
R$_1$' is azide, halogen, or alkoxy;
(b) transforming Compound III with hydrazine into a 2-deoxy-ribose compound of the formula IV $$\begin{array}{c} CHO \\ \vdash R_1' \\ \vdash OH \\ \vdash OH \\ CH_2OH \end{array} \quad (IV)$$

(c) converting the 2-deoxy-ribose compound IV with methanol in the presence of a strong acid into a 1-O-methylglucoside of the formula V

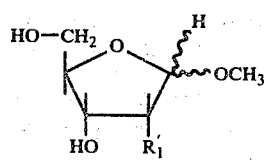

(d) reacting the glucoside V with acetic anhydride, in a polar organic solvent, (particularly pyridine) to form a 1-O-methyl-ribose-3,5-diacetate of formula VI.

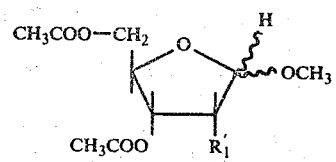

(e) converting the diacetate VI with acetic anhydride in glacial acetic acid, in the presence of a strong acid (particularly sulfuric acid) into a ribose-1,3,5-triacetate of formula VII

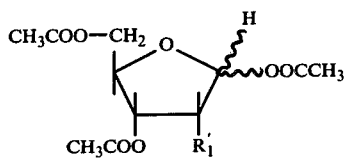

(VII)

(f) condensing the obtained triacetate with a purine base wherein the free primary amino group is protected by acylation, in an organic solvent in the presence of Lewis acid and deacylating the product obtained to yield a compound of formula I in which $R_1$ is azide, halogen, or alkoxy;

(g) optionally separating the product obtained into its α and β anomers; and (h) optionally reacting Compound I in which $R_1$ is azido with triphenylphosphine in saturated methanolic ammonia, into the corresponding Compound I where $R_1$ is amino.

In step (a) above, introduction of the azide or halogen is carried out in conventional fashion. The alkoxy group may be introduced with an alkylating agent such as diazomethane, diazoethane or benzyl halide, to yield the uridine where $R_1'$ is alkoxy.

When $R_1$ is halogen, i.e., fluoro, chloro, bromo, or iodo, fluoro and chloro are preferred. When $R_1$ is a small alkoxy group, 1 to 6 carbon atoms is preferred. A particularly desirable alkoxy group is methoxy.

The purine bases utilizable in step (f) may be adenine, guanine, inosine, 2-amino-purine, 2,6-diamino-purine, 6-mercaptopurine, 6-methylmercaptopurine, 6-mercaptoguanine, 6-methylmercaptoguanine; guanine and adenine are preferred.

The multi-step process of the invention provides the desired product in high yields. Thus, 9-(2'azido-2'-deoxy-α-D-ribofuranosyl)-adenine, 9-(2'-azido-2'-deoxy-β-D-ribofuranosyl)-adenine, 9-(2'-azido-2'-deoxy-β-D-ribofuranosyl)-guanine and 7-(2'-azido-2'-deoxy-β-D-ribofuranosyl)-guanine were obtained in yields, relative to uridine as the base material, of 3.2%, 7.0%, 3.9% and 2.7%, respectively. The corresponding aminonucleosides are obtained with yields of 2.6%, 6.8%, 3.5% and 2.6%, respectively.

The 5'-phosphates of the available purine derivatives according to the process of the invention are similarly obtained following the methods described by F. Eckstein, M. Goumet and R. Wetzel in *Nucleic Acids Research*, 2 (1975), pages 1771–1775. Of these 5'-phosphates, the corresponding di- and triphosphates may be produced following the method described by A. M. Michelson (Biochem. Biophys. Acta 91 (1964), pages 1–13).

In step (a) of the process of the invention, 2'-azido compounds are formed preferably by reacting uridine with diphenylcarbonate in hexamethylphosphoric triamide at elevated temperature, e.g. at 140° C., in the presence of a little sodium bicarbonate, and then reacting the mixture at high temperature with lithium azide.

To implement step (b), Compound III is mixed in an aqueous hydrazine hydrate solution at a temperature between 40° C. and 80° C. or, ideally, at approximately 65° C.; the evaporated reaction product re-combined with water is treated with benzaldehyde and heated in a bath of boiling water while being mixed.

In step (c) the use of sulfuric acid is recommended as the strong acid and the reaction is preferably carried out at a temperature between 0° C. and 10° C. or, most preferably, at a temperature between 3° C. and 5° C.

In step (f) of the process of the invention, $N^6$-octanoyladenine or $N^2$-palmitoylguanine is best used as a protected purine base while 1,2-dichlorethane is used as an organic solvent with stannic tetrachloride serving as Lewis acid. The acyl protective group is finally split with sodium methylate in methanol.

Highly desirable new compounds which may be used directly as medicine or as intermediate products for producing medically active material are listed below.

2-azido-2-deoxyribose.
2-azido-2-deoxyribose-1-O-methyl-glucoside.
1-O-methyl-2-azido-2-deoxyribose-3,5-diacetate.
2-azido-2-deoxyribose-1,3,5-triacetate.
9-(2'-azido-2'-deoxy-α-D-ribofuranosyl)-adenine.
9-(2'-azido-2'-deoxy-β-D-ribofuranosyl)-guanine.
7-(2'-azido-2'-deoxy-β-D-ribofuranosyl)-guanine.
9-(2'-amino-2'-deoxy-β-D-ribofuranosyl)-guanine.
7-(2'-amino-2'-deoxy-β-D-ribofuranosyl)-guanine.

2'-fluoro-2'-deoxy and 2'-O-methyl-2'-deoxyuridine have already been disclosed (J. F. Codington, I. L. Doerr, J. J. Fox, J. Org. Chem. 29 (1964), pages 558–564, and D. M. G. Martin, C. B. Reese, G. F. Stephenson, Biochemistry 7 (1968), pages 1406–1412).

The following examples are illustrative.

The melting points indicated were not corrected, the IR-spectra were registered using a Perkin-Elmer spectrometer (model 137), the UV-spectra using a Shimadzu spectrometer (model UV 200) and a Zeiss spectrometer (PMQ II), the NMR-spectra using a Bruker-Physik spectrometer (HFX 60) and the CD-spectra using a Cary spectrometer (61). The chemical displacements are indicated as δ-values in ppm, relative to the internal standard tetramethylsilane.

The thin-layer chromatographic examinations (Merck-Silica Gel 60 F 254) were conducted on plates coated with a layer thickness of 0.2 mm using solvent Systems A (methanol/chloroform, 2/8 (volume/volume)) or B (ethanol/monomolar ammonium acetate solution, 7/3 (volume/volume)) or the solvent systems indicated. The preparatory thin-layer chromatography was conducted on plates coated with a layer thickness of 2 mm, produced by the same manufacturer (60 F 254). For the column chromatography, Silica gel was used (Merck Silica Gel 60 (0.063 to 0.2 mm)). The ion exchangers used (Dowex 1 × 2 and 1 × 4) were obtained in chloride form from the supplier firm (Serva Feinbiochemica) and thoroughly treated with an excess quantity of aqueous hydroxide solution and then neutralized by rinsing.

The electrophoresis was conducted using the mentioned buffers (as indicated) for a period of 90 minutes at 30 v/min.

For the paper chromatography, a washed paper (Schleicher and Schull 2043 b) was used, the solvent System B or the correspondingly indicated solvent system being used.

The products $N^6$-octanoyladenine and $N^2$-palmitoylguanine used according to the instant invention were essentially obtained according to the methods of Furukawa and Honjo (Chem. Pharm. Bull (Japan) 16 (1968), pages 1076–1080).

EXAMPLE 1

Step (a)

2-azido-2'-deoxyuridine (III) was prepared using a modified version of the method established by Verheyden et al. (J. Org. Chem. 36 (1971), pp. 250–254). 10 g of uridine (Formula II) were heated with 12 g of diphenylcarbonate in 80 ml of hexamethylphosphoric acid triamide to 140° C. while stirring in an oil bath 0.24 g of sodium bicarbonate. When the frothing subsided (approx. 30 minutes), 8 g of lithium azide were added to the solution which was heated for another two hours. The thin-layer chromatogram of the solvent System A indicated that the $O^2$, 2'-cyclouridine appearing as intermediate product had virtually disappeared and that the desired compound was now present as main product. The solution was then cooled, diluted with 160 ml of water and twice extracted with 200 ml of chloroform. The combined chloroform solutions were twice re-extracted with 160 ml of water, whereupon the combined aqueous phases were re-extracted with three times in 200 ml chloroform. The solution was then evaporated in a vacuum as thoroughly as possible. The residue was well stirred with a mixture of 160 ml of acetone and 60 ml of methanol, filtered off and evaporated whereupon the remaining oil was applied to a column loaded with 700 g of silica gel, which was previously equilibriated with acetone. The column was eluted with acetone and then the fractions containing the product were evaporated, combined and placed on 6 preparatory thin layer plates (2 mm silica gel plates, 20 × 40 cm). These thin-layer chromatographic plates were developed with an acetone/ethylacetate mixture (1/1, volume/volume), the product-containing bands were dissolved and were eluted with acetone. The acetone was then evaporated and the residue was dissolved in 45 ml of pyridine and filtered in order to remove all traces of silicon dioxide. The pyridine was evaporated, and the pyridine traces were removed by the addition and evaporation of water, and the product obtained was in the form of a yellow resin which, according to solvent System A and the aforementioned acetone/ethylacetate solvent mixture proved to be homogeneous in terms of thin-layer chromatography. Yield — 5.49 g = 50%.

Without further purification this material was used to continue the process further. The resin crystallized promptly when kept at 4° C.

When preparing the analysis test sample in order to remove the yellow color the obtained 2'-azido-2'-deoxyuridine was applied to a column filled with an ionic exchanger in OH form (Dowex 1 × 4). The column was then eluted with water and 50% methanol and finally with a solution of 0.1 m triethyl ammonium bicarbonate, the desired material being washed out together with a small amount of inorganic salts. The solution was then evaporated, whereupon traces of the triethylamine were removed by a methanol evaporation process. The residue was stirred with acetone; the acetone was evaporated; and the residue was conducted over a small column corresponding to the above column, filled with silica gel, and was eluted with acetone. By means of evaporation, the product was obtained in the form of a stiff, clear resin which, when scratched, crystallized into white needles which melted at 139° C. and 147° C. as they darkened and disintegrated, these processes taking place very rapidly at temperatures above 180° C.

Analysis: $C_9H_{11}N_5O_5$: Calculated: C, 40.15; H, 4.12; N, 26.02%. Obtained: C, 40.51; H, 3.80; N, 26.15%.

IR-spectrum (resin layer) = 2120 cm$^{-1}$.

The NMR-spectrum (D$^6$-DMSO) was identical to that shown in the text material (ref. Verheyden et al., loc. cit.).

Step (b)

2-azido-2-deoxyribose (IV)

2.54 g of 2'-azido-2'-deoxyuridine was dissolved in 250 ml of a 15% hydrazine hydrate solution and heated in an oil bath while stirring for a period of one hour to 65° C. Upon expiration of this time, the thin-layer chromatogram of the solvent System A indicated the total disappearance of the starting material. The solution was evaporated in a vacuum and yielded an orange-colored resin which was dissolved in 100 ml of water. 10 ml of benzaldehyde was added and the mixture heated during constant stirring for a period of 8 minutes in a boiling water bath. The solution was then rapidly cooled to below room temperature and a glutinous precipitate was filtered off, consisting mainly of benzaldehydeazine. The filtrate was then extracted with three times 100 ml of ether. The aqueous solution was evaporated and the residue was dissolved in a minimal amount of methanol. The solution was then applied to a silica gel column (2.3 × 32 cm) prepared with chloroform. The column was eluted with 100 ml fractions of chloroform (200 ml), 700 ml of a 5% solution of methanol in chloroform and with 600 ml of a 10% solution of methanol in chloroform. The desired product was found in the fractions 9 to 13 and was identified by examining each fraction by means of thin-layer chromatography, by the solvent System A, and sprayed on plates with a solution of aniline phosphate (17 ml of n-butanol, 6 ml of water, 0.36 ml of aniline and 0.28 ml of 85% phosphoric acid), and, finally, heated for a period of ten minutes in a drier at 110° C. The 2-azido-2-deoxyribose emerged as a reddish-brown stain with an $R_f$ value of 0.5. The fractions containing the product were combined and evaporated to a colorless resin (1.053 g, yield = 64%), which did not crystallize.

Analysis: $C_5H_9N_3O_4$: Calculated: C, 34.29; H, 5.18; N, 23.99%. Obtained: C, 34.45; H, 5.07; N, 23.60%.

IR-spectrum (liquid film): 3270 cm$^{-1}$ (—OH) and 2100 cm$^{-1}$ (—N$_3$).

NMR-spectrum (D$_2$O): δ = 3.37 to 4.50 (5H, complex pattern of H-2, H-3, H-4 and H$_{a,b}$-5 of the furanose and pyranose forms), 4.96 (0,2H, J$_{12}$ = 2 Hz), 4.97 (0,6 H, J$_{12}$ = 7.5 Hz), 5.28 (0,1H, J$_{12}$ = 2.5 Hz), 5.53 (0,1H, J$_{12}$ = 4 Hz), (H-1 α- and β-anomers of pyranose, β- and α-anomers of furanose, respectively).

Step (c)

2-azido-2-deoxyribose-1-O-methyl-glucoside (V)

1.021 g of 2-azido-2-deoxyribose was dissolved in 15 ml of dry methanol and cooled to 0° C. Then 0.075 ml of concentrated sulfuric acid was added and the reaction mixture was stored in the refrigerator for 5 days at 3° C. to 5° C. The reaction progress was followed by thin-layer chromatography, with solvent System A. The product emerged in the form of a greyish-brown stain with an $R_f$ value of 0,7, if the thin-layer plate was sprayed with the aforementioned aniline phosphate solution and heated to 110° C. for an extended period of time since the stain would not attain its full intensity until it had undergone over-night treatment. After a period of 5 days, 2 ml of pyridine was added, the mixture was evaporated to dryness, the residue was dissolved in the minimum amount of methanol and the solution was applied to a column (1.7 × 24 cm) loaded with silica gel and prepared with chloroform. The column was eluted with 300 ml chloroform and 700 ml of a 3% methanol solution in chloroform and collected in 50 ml fractions. The fractions 10 to 17 contained a material yielding a single spot on the aforementioned thin-layer chromatogram. The fractions containing the product were combined and evaporated, resulting in a colorless resin which did not crystallize (0.74 g, yield = 67%).

Analysis: $C_6H_{11}N_3O_4$: Calculated: C, 38.09; H, 5.86; N, 22.21%. Obtained: C, 38.11; H, 6.01; N, 22.24%.

IR-spectrum (liquid film): 3300 cm$^{-1}$ (—OH), 2910 cm$^{-1}$ (—CH$_3$) and 2110 cm$^{-1}$ (—N$_3$).

NMR-spectrum (d$^6$-DMSO): $\delta$ = 3.24, 3.21 (3H, two singlets, methoxy signals of $\beta$- or $\alpha$-anomers 3.33 to 4.0 (4H, complex multiplet, $H_{a,b}$-5 with a center at $\delta$ = 3,48, H-4, H-2), 4.21 (1H, q, H-3, $J_{23} = J_{34} = 5.5$ Hz), 4.68 (1H, t, OH-5), 4.69 (0,85H, s, H-1 of the $\beta$-anomer), 4.97 (0,15H, d, $J_{12} = 4.5$ Hz, H-1 of the $\alpha$-anomer), 5.60 (1H, d, OH-3).

Step (d)

1-O-methyl-2-azido-2-deoxyribose-3,5-diacetate (VI)

0.666 g of 2-azido-2-deoxyribose-1-O-methyl-glucoside was dissolved in 10 ml of pyridine and 4 ml of acetic acid anydride was added. After allowing to stand over-night at room temperature, the solvent had evaporated. The residue was dissolved in 80 ml of chloroform and rinsed three times with 20 ml of water. The chloroform phase was separated, and dried with anhydrous magnesium sulphate. Then, it was filtered and evaporated and the product obtained in the form of a colorless resin (0.893 g, yield = 93%), which yielded a single spot with an R$_f$ value of 0.91 on the thin-layer chromatogram (ethylacetate/diethylether (1/1 volume/volume) developed by spraying with the aniline phosphate solution).

Analysis: $C_{10}H_{15}N_3O_6$: Calculated: C, 43.96; H, 5.53; N, 15.38%. Obtained: C, 44.11; H, 5.38; N, 15.36%.

IR-spectrum (liquid film): 2890 cm$^{-1}$ (—CH$_3$), 2100 cm$^{-1}$ (—N$_3$), 1740 cm$^{-1}$ (carbonyl) and 1360 cm$^{-1}$ (CH$_3$CO—).

NMR-spectrum (CDCl$_3$): $\delta$ = 2,06 (3H, s), 2.15 (3H, s), 3.35, 3.47 (3H, 2 singlets, methoxyl signals of $\beta$- or $\alpha$-anomer, 3.57 to 4.5 (4H, complex pattern, H-4 with center at $\delta$ = 4.25, H-2, $H_{a,b}$-5), 4.83 (0.85H, 3, H-1 of $\beta$-anomer), 5.08 (0.15H, d, $J_{12}$ = 4.5 Hz, H-1 of $\alpha$-anomer) and 5.26 (1H, t, H-3, $J_{23} = J_{34} = 5.5$ Hz).

Step (e)

2-azido-2-deoxyribose-1,3,5-triacetate (VII)

0.87 g 1-O-methyl-2-azido-2-deoxyribose-3,5-diacetate was dissolved in 4.5 ml of glacial acetic acid and 1.2 ml of acetic acid anhydride and was cooled to 0° C. Then 0.23 ml of sulfuric acid concentrate was gradually added while stirring briskly. After adding the concentrate, the solution was allowed to warm to room temperature and to stand for a period of 22 hours and it (the solution) changed to dark red. 6.25 g of ice was then added to the mixture and same was extracted with 4 × 13 ml chloroform. The chloroform phases were combined, and rinsed with a saturated sodium bicarbonate solution (2 × 25 ml) and with 25 ml of water, dried over anhydrous magnesium sulphate, then filtered and evaporated to dryness so that the product obtained was in the form of a colorless resin (0.889 g, yield = 93%) which showed on the thin-layer chromatogram (ethylacetate/diethylether 1/1 (volume/volume)) an R$_f$ value (0,89) similar to that of the starting material whose NMR-spectrum, however, indicated the total disappearance of the methoxy signal.

Analysis: $C_{11}H_{15}N_3O_7$: Calculated: C, 43.86; H, 5.02; N, 13.95%. Obtained: C, 44.17; H, 4.91; N, 13.82%.

IR-spectrum (liquid film): 2920 cm$^{-1}$ (—CH$_3$), 2110 cm$^{-1}$ (—N$_3$), 1745 cm$^{-1}$ (carbonyl) and 1360 cm$^{-1}$ (CH$_3$CO).

NMR-spectrum (CDCl$_3$): $\delta$ = 2.10 (4.1H, s), 2.20 (4,9H, s), 3.6 to 4.5 (4H, complex pattern, H-4 with center at $\delta$ = 4.30, H-2, $H_{a,b}$-5), 5.27 (1H, m, H-3), 6.09 (0.6H, s, H-1 of $\beta$-anomer) and 6.43 (0,4H, d, $J_{12}$ = 4.5Hz, H-1 of $\alpha$-anomer).

Steps (f) and (g)

9-(2'-azido-2-deoxyribofuranosyl)-adenine ($\alpha$- and $\beta$-anomer; I, R$_1$ = N$_3$ and R$_2$ = 9-adenyl)

515 mg of 2-azido-2-deoxyribose-1,3,5-triacetate was dissolved in 40 ml of 1,2-dichloroethane and 590 mg of N$^6$-octanoyladenine was added. The mixture was heated to boiling at reflux and then 588 mg (0.27 ml) of stannous tetrachloride was added. After heating for 6 hours under reflux boiling, an additional 0.07 ml of stannous tetrachloride was added. After 9 hours the solid material had dissolved completely and the mixture had a dark coloration. Using solvent System A, the thin-layer chromatogram showed a large spot which migrated with the solvent front, and a spot of unconverted octanoyladenine (R$_f$ value = 0.74). The solution was evaporated and the residue dissolved in 8 ml 2n sodium methoxide solution and 28 ml methanol. After allowing to stand for a period of ten hours at 37° C., the de-acylation process was completed and the thin-layer chromatogram of solvent System A, essentially only indicated the $\alpha$- and $\beta$-anomers of the product (R$_f$ values—0.42 and 0.55). The solution was evaporated and the residue dissolved in a 10% methanol/water solution, the solution applied to a column loaded with an ion exchanger (2.1 × 30 cm) in the OH-form (Dowex 1 × 4), and same rinsed in water with a solution of 30% methanol, the products being eluted with a 50% methanol solution in water. The $\alpha$-anomer was eluted first. Since the separation was incomplete, an additional overpass over the ion exchanger column (Dowex 1 × 4, OH—) was necessary so that the $\alpha$-anomer (4350 A$_{260}$-units, yield = 17%) was obtained and the $\beta$-anomer (9700 A$_{260}$-units, yield = 38%), as well as a small amount of unseparated fraction (1050 A$_{260}$-units, yield = 4% which mostly consisted of the $\alpha$-anomer). Total yield = 15100 A$_{260}$-units = 59%. By evaporating the solution, 9-(2'-azido-2'-deoxy-$\beta$-D-ribofuranosyl)-adenine ($\beta$-A$_z$) in crystalline form was obtained. The material may be dissolved and re-crystallized from water. Melting point = 217° C. to 220° C. (decomposition); published melting point (Mengel and Wiedner, loc. cit.) = 205° C.

$\lambda_{max}^{H_2O}$ = 259.5 nm ($\epsilon$ = 14900), $\lambda_{max}^{pH1}$ = 257 nm nm ($\epsilon$ = 14500). The NMR-spectrum (d$^6$-DMSO) was identical to that of the literary passage (patent) of Mengel and Wiedner (loc. cit.).

9-(2'-azido-2'-deoxy-$\alpha$-D-ribofuranosyl) adenine ($\alpha$-Az) was obtained in the form of a colorless resin which gradually crystallized from acetone. Melting point = 171° to 173° C. (decomposition).

Analysis: $C_{10}H_{12}N_8O_3$ (MG = 292.3): Calculated: C, 41.10; H, 4.14; N, 38.34%. Obtained: C, 41.44; H, 4.31; N, 38.02%.

IR-spectrum (KBr) = 3300 to 3050 cm$^{-1}$ (OH, NH$_2$), 2120 cm$^{-1}$ (N$_3$), 1690, 1640 and 1600 cm$^{-1}$ (NH, purine).

UV-spectrum: $\lambda_{max}^{H_2O}$ = 259.5 nm ($\epsilon$ = 14900), $\lambda_{max}^{pH1}$ = 257.5 nm ($\epsilon$ = 14400).

NMR-spectrum (d$^6$-DMSO) = 3.59 (2H, d, H$_{a,b}$-5′), 4.12 (1H, m, H-4′), 4.56 (2H, m, H-2′ and H-3′), 4.95 (1H, t, OH-5′), 6.24 (1H, d, OH-3′), 6.39 (1H, d, J$_{1'2'}$ = 5 Hz, H-1′), 7.28 (2H, s, —NH$_2$), 8.13 and 8.24 (2H, s, H-2 and H-8).

The electrophoretic mobilities in a 0.1 m borate solution with a pH value of 10 were as follows: $\beta$-A$_z$ = 0.6 cm; $\alpha$-A$_z$ = 0.5 cm; adenosine = 7.6 cm. The R$_f$ values on paper, using solvent System B, were as follows: $\beta$-A$_z$ = 0.73; $\alpha$-A$_z$ = 0.76 and adenosine = 0.66.

Step (h)

9-(2′-amino-2′-deoxy-$\beta$-D-ribofuranosyl)-adenine (I, R$_1$ = NH$_2$ and R$_2$ = 9-adenyl). 37.9 mg of 9-(2′-azido-2′-deoxy-$\beta$-D-ribofuranosyl)-adenine was dissolved in 0.9 ml of dry pyridine and 0.9 ml of a 50% saturated methanolic ammonia solution, and 92 mg of triphenylphosphine were added. After keeping over-night at room temperature, the thin-layer chromatogram, of solvent System B showed a virtually quantitative conversion of the starting material (R$_f$-value = 0,83) into a product with an R$_f$ value of 0.57. The solution was evaporated and the residue was dispersed between benzene and water. The aqueous layer was separated, the benzene layer was washed with water, and the combined aqueous solutions were evaporated. The residue was again dissolved in water and the solution was applied to an ion exchanger column in OH-form (Dowex 1 × 4, 1.2 × 16 cm). The desired product was obtained by eluting with water (1800 A$_{260}$-units, yield = 96%). The aqueous solution was evaporated and the residue was re-crystallized from dry acetonitrile. White crystals were obtained with a melting point of 199.5° to 201° C.; published melting point (Wolfrom and Winkley, loc. cit.) = 194° to 196° C.

9-(2′-amino-2′-deoxy-$\alpha$-D-ribofuranosyl)-adenine 81.4 mg of 9-(2′-azido-2′-deoxy-$\alpha$-D-ribofuranosyl)-adenine was dissolved in 2 ml of dry pyridine and 2 ml of 50% saturated methanolic ammonia solution, and 196 mg of triphenylphosphine were added. The starting material had an R$_f$-value of 0.75 with thin-layer chromatography, using System B. After being allowed to stand overnight, the starting material was virtually quantitatively converted into a new material (having an R$_f$-value of 0.5). The solution was evaporated and the residue was triturated with a benzene/ether mixture (1/1 (50 ml in three portions)) and then the material was dissolved with water and was conducted through a column with an ion exchanger in the OH-form (Dowex 1 × 2, 1.6 × 17 cm). By eluting with water, a homogeneous product was obtained (3540 A$_{260}$-units, yield = 84%) which is re-crystallized from an ethanol/water mixture into white crystals. Melting point = 148° to 149° C.). Literary melting point (Wolfrom and Winkley, loc. cit.) amounts to 149° to 151° C.

EXAMPLE 2

Steps (f) and (g)

7-(2′-azido-2′-deoxy-$\beta$-D-ribofuranosyl)-guanine (I, R$_1$ = N$_3$ and R$_2$ = 7-guanyl) and 9-(2′-azido-2′-deoxy-$\beta$-D-ribofuranosyl)-guanine (I, R$_1$ = N$_3$ and R$_2$ = 9-guanyl)

689 mg of 2-azido-2-deoxyribose-1,3,5-triacetate in 50 ml of 1,2-dichloro-ethane were dissolved and 1.11 g N$^2$ palmitoylguanine were added thereto. The mixture was heated to reflux boiling and then 0.34 ml of stannous tetrachloride were added. After heating for about 90 minutes to boiling under reflux, the solid material completely dissolved and the thin-layer chromatogram showed two spots running close together at the solvent front and unconsumed N$^2$-palmitoylguanine (R$_f$-value = 0.67, strip-like). The solution was cooled to room temperature and evaporated. The resulting resin obtained is dissolved in chloroform and then applied to a silica gel column prepared with chloroform (2.2 × 36 cm). The column was washed with 400 ml of chloroform and eluted with 600 ml of a 3% methanol solution in chloroform. The fractions are then combined containing a material, which, when using solvent System A, is more rapidly washed out than palmitoylguanine. The resulting material is evaporated to a light brown resin (1.32 g), which was dissolved in 10 ml of a 2n sodium methoxide solution and 40 ml of methanol. It was then allowed to stand overnight at 37° C., whereupon the deacylation process was completed (thin-layer chromatography, solvent System A). The solution was evaporated and the residue suspended in water and the material is then applied to a column filled with an ion exchanger resin column in OH-form (Dowex 1 × 2, 2.2 × 36 cm), then thoroughly rinsed with water and washed out with a 0.1 triethylammonium bicarbonate solution in order to remove the firmly absorbed inorganic salts. The products are eluted in the form of a single peak with a 0.4 m triethylammonium bicarbonate solution. The peak will contain 12310 A$_{253.5}$-units, which indicates that approximately 0.57 mmol of the 7-(2′-azido-2′-deoxy-ribofuranosyl)guanine-isomers and approximately 0.71 mmol of the 9-(2′-azido-2′-deoxy-ribofuranosyl)-guanine-isomers have formed (this conclusion is based on the assumption that the $\alpha$- and $\beta$-anomers of these compounds have the same $\lambda_{max}^{H_2O}$-values and extinction coefficients). The condensation yields 1.29 mmol of the nucleotide, which corresponds to a total yield of the condensation of 56.5%. The solution is evaporated to dryness, traces of triethylamine are removed by the addition of methanol and evaporation of the methanol. The residue is then dissolved in approximately 250 ml of boiling water. The solution, allowed to cool at room temperature, will form a crystalline precipitate which is collected and will recrystallize again from boiling water, whereby 102.3 mg (yield = 14.6%, relative to ribose triacetate) 7-(2′-azido-2′-deoxy-$\beta$-D-ribofuranosyl)-guanine (7-$\beta$-G$_z$) are obtained in the form of white crystals which turn dark above 238° C., and have no melting point of less than 300° C.

Analysis: $C_{10}H_{12}N_8O_4$ (MG = 308,3): Calculated: C, 38.96; H, 3.92; N, 36.35%. Obtained: C, 38.91; H, 3.92; N, 36.39%.

IR-spectrum: (KBr) = 3350–3100 cm$^{-1}$ (OH, NH$_2$), 2850, 2650 cm$^{-1}$ (NH), 2120 cm$^{-1}$ (N$_3$), 1670, 1620, 1560 and 1460 cm$^{-1}$ (NH, CO, purine).

UV-spectrum: $\lambda_{max}^{H_2O} = 285.5$ nm ($\epsilon = 7600$), 240 nm (sh) ($\epsilon = 6600$), 216 nm ($\epsilon = 20100$); $\lambda_{max}^{pH1} = 250$ nm ($\epsilon = 9400$), 270 nm (sh) ($\epsilon = 6700$); $\lambda_{max}^{pH13} = 282$ nm ($\epsilon = 6400$), 240 nm (sh) ($\epsilon = 7600$).

NMR-spectrum (d$^6$-DMSO): $\delta = 3.63$ (2H, m, H$_{a,b}$-5'), 3.92 (1H, m, H-4'), 4.13–4.53 (2H, m, H-2' and H-3'), 5.07 (1H, t, OH-5'), 5.90 (1H, d, OH-3'), 6.15 (1H, d, J$_{1'2'} = 5.0$ Hz, H-1'), 6.22 (2H, s, —NH$_2$) and 8.32 (1H, s, H-8).

By evaporation of the mother liquor volume to approximately one-half and additional storage at room temperature, a further precipitate will form, appearing as white crystals (149.3 mg, yield = 21%, relative to ribose triacetate), resulting in practically pure 9-(2'-azido-2'-deoxy-β-D-ribofuranosyl)-guanine (9-β-Gz). Melting point = 206° C. (decomposition).

Analysis: $C_{10}H_{12}N_8O_4$ (MG = 308,3): Calculated: C, 38.96; H, 3.92; N, 36.35%. Obtained: C, 38.84; H, 4.18; N, 36.31%.

IR-spectrum: (KBr) = 3400–3150 cm$^{-1}$ (OH, NH$_2$), 2900, 2700 cm$^{-1}$ (NH), 2120 cm$^{-1}$ (N$_3$), 1710, 1690, 1630, 1600, 1530 and 1480 cm$^{-1}$ (NH, CO, purine).

UV-spectrum: $\lambda_{max}^{H_2O} = 253$ nm ($\epsilon = 13700$), 270 nm (sh) ($\epsilon = 9800$); $\lambda_{max}^{pH1} = 257.5$ nm ($\epsilon = 12000$), 280 nm (sh) ($\epsilon = 7900$); $\lambda_{max}^{pH13} = 258–268$ ($\epsilon = 11600$).

NMR-spectrum (d$^6$-DMSO): $\delta = 3.58$ (2H, m, H$_{a,b}$-5'), 3.91 (1H, m, H-4'), 4.32–4,58 (2H, m, H-2' and H-3'), 5.05 (1H, t, OH-5'), 5.81 (1H, d, J$_{1'2'} = 5.5$ Hz, H-1'), 5.97 (1H, d, OH-3'), 6.48 (2H, s, —NH$_2$) and 7.94 (1H, s, H-8).

The electrophoretic mobilities in 0.1 m borate solution, pH-value = 10, are as follows: 7-β-G$_z$ = 4.2 cm; 9-β-G$_z$ = 5.8 cm; guanosine = 11.6 cm. The R$_f$-values on paper, using solvent System B, are as follows: 7-β-G$_z$ = 0.60; 9-β-G$_z$ = 0.71 and guanosine = 0.60.

After the mother liquor is evaporated, examination of the residue will reveal through the NMR-spectrum (d$^G$-DMSO) H-8-signals at $\delta$ = 7.86, 7.94, 8.08 and 8.32 at a ratio of 25:45:40:16, a diffused doublet which is most likely composed of two virtually superimposed doublets, J$_{1'2'}$-5Hz at $\delta$ = 6.17, and another doublet at $\delta$ = 6.56 (J$_{1'2'}$ = 4.5 Hz), the additional signals being probably a result of the compound 7-α-G$_z$ (at 8.08 and 6.56) and of the compound 9-α-G$_z$ (at 7.86 and 6.17). The distribution of the condensation products is therefore as follows: 12% 7-α-G$_z$; 30% 7-β-G$_z$; 7% 9-α-G$_z$; and 51% 9-β-G$_z$. The ratio of the 7-isomers to the 9-isomers were 42:58 (cf. the estimated result of 45:55 as per the UV-spectrum).

Step (h)

9-(2'-amino-2'-deoxy-β-D-ribofuranosyl)-guanine (9-β-Ga) (I) (R$_1$ = NH$_2$ and R$_2$ = 9-guanyl)

35.2 mg of 9-(2'-azido-2'-deoxy-β-D-ribofuranosyl)-guanine were dissolved in 1 ml of dry pyridine and 1 ml of 50% saturated ammonia solution in methanol and 92 mg of triphenylphosphine were added. The solution was stirred overnight then transferred quantitatively with aqueous methanol into a larger flask and evaporated. The residue was triturated with a diethylether/benzene mixture (1/1, volume/volume; 3 portions, total volume = 25 ml) and filtered off. The remaining solid products were filtered and dried 28.7 mg of the product being obtained (yield = 89%). Using the thin-layer chromatography process with solvent System B, this material yields a single spot with an R$_f$-value of 0.38 (the base material indicated an R$_f$-value of 0.76). Melting point = 217° to 219° C.

Analysis: $C_{10}H_{14}N_6O_4$ (MG = 282.3): Calculated: C, 42.55; H, 5.00; N, 29.78%. Obtained: C, 43.23; H, 5.31; N, 29.73%.

IR-spectrum: (KBr) — 3400–3050 cm$^{-1}$ (OH, NH$_2$), 2890, 2710 cm$^{-1}$ (NH), 1720, 1690, 1630, 1600, 1540, 1530 and 1480 cm$^{-1}$ (NH, CO, purine).

UV-spectrum: $\lambda_{max}^{H_2O} = 253$ nm ($\epsilon = 13200$).

NMR-spectrum (6-DMSO): $\delta = 3.28$ (2H, s, —NH$_2$-2'), 3.40–4.05 (5H, m, H-2', H-3', H-4', 5H$_{a,b}$-5'), 5.00 (1H, broad s, OH-5'?), 5.46 (1H, d, J$_{1'2'}$ = 8 Hz, H-1'), 6.40 (2H, s, —NH$_2$) and 7.84 (1H, s, H-8).

The electrophoretic mobility in a 0.1 m borate solution at a pH value of 10 was as follows: 9-β-Ga = 6.7 cm guanosine = 11.7 cm. In a 0.05 m ammonium formate solution with a pH value of 3.5, the following values result: 9-β-Ga = 14.6 cm, guanosine = 4.6 cm. The R$_f$-values on paper, using solvent System B, were as follows: 9-β-Ga = 0.54 and guanosine = 0.60.

7-(2'-amino-2'-deoxy-β-D-ribofuranosyl)guanine (7-β-Ga, (I, R$_1$ = NH$_2$ and R$_2$ = 7-guanyl).

This material was prepared according to the method described for the 9-β-Ga compound, starting with 31.4 mg 7-(2'-azido-2'-deoxy-β-D-ribofuranosyl)-guanine, 28 mg of the product being obtained (yield = 97%) which gradually turns dark at a temperature above 220° C. and decomposes at above 250° C. The material had no melting point below 300° C. The thin-layer chromatogram, using solvent System B, showed a single elongated stain with an R$_f$-value of 0.35.

Analysis: $C_{10}H_{14}N_6O_4$ (MG = 282.3): Calculated C, 42.55; H, 5.00; N, 29.78%. Obtained: C, 42.54; H, 5.14; N, 29.77%.

IR-spectrum: (KBr) = 3400–3100 cm$^{-1}$ (OH, NH$_2$), 2880, 2650 cm$^{-1}$ (NH), 1660, 1560 and 1470 cm$^{-1}$ (NH, CO, purine).

UV-spectrum: $\lambda H_2O = 285.5$ nm ($\epsilon = 7700$).

NMR-spectrum (d$^6$-DMSO): 3.30 (3H, broad s, —NH$_2$-2' + HO?), 3.42–4.07 (5H, m, H-2', H-3', H-4', H$_{a,b}$-5'), 4.94 (1H, broad s, OH-5'?), 5.73 (1H, d, J$_{1'2'}$ = 7,5 Hz, H-1'), 6.17 (2H, s, —NH$_2$) and 8.17 (1H, s, H-8).

The electrophoretic mobility of a 0.1 m borate solution having a pH value of 10 was as follows: 7-β-Ga = 6.1 cm guanosine = 11.7 cm. The following values result for a 0.05 m ammonium formate solution having a pH value of 5: 7-β-Ga = 16.2 cm and guanosine = 4.6 cm. The R$_f$-vlaues on paper, using solvent System B, were as follows: 7-β-Ga = 0.49 and guanosine = 0.60.

EXAMPLE 3

Synthesis of 2'-deoxy-2'-azido-ribofuranosyl purine-5'-phosphates.

The phosphorylation of the azido-derivatives can be done with phosphoroxychloride in the manner described for 2'-deoxy-2'-azido-uridine (J. Hobbs, H. Sternbach, M. Sprinzl and F. Eckstein, Biochemistry 12 (1973). pp. 5138–5145, or Eckstein, Goumet and Wetzel, loc.cit.), wherein the additional phosphorylation of the di- and tri-phosphates takes place according to the process of Michelson (A. M. Michelson, Biochemica Biophysica Acta 91 (1964), pp. 1–16).

EXAMPLE 4

Synthesis of 2'-deoxy-2'-amino-ribofuranosyl purine-5'-phosphates

These compounds are obtained by hydrogenation of the corresponding azido-derivatives with 10% palladium on active carbon according to the process of Hobbs, Sternbach, M. Sprinzl and F. Eckstein (loc.cit.), or according to the method of Mungall, Greene, Heavner and Letsinger (W. S. Mungall, G. L. Greene, E. A. Heavner and R. L. Letsinger, J. Org. Chem. 40 (1975), pp. 1659-1662).

It will be understood that the specification and examples are illustrative but not limitative of the present invention and that other embodiments within the spirit and scope of the invention will suggest themselves to those skilled in the art.

What is claimed is:

1. Process for the preparation of a 2'-substituted-D-ribofuranosyl purine compound of the formula

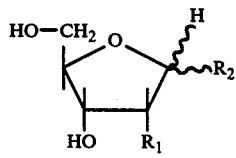

in which
$R_1$ is azide, amino, halogen or alkoxy, and
$R_2$ is the residue of a purine base and particularly a 9-adenyl group, a 7-guanyl group, or a 9-guanyl group (the waved lines in formula I above show that $R_2$ can be bound in the α- or β-configuration), which process comprises (a) converting a uridine of the formula

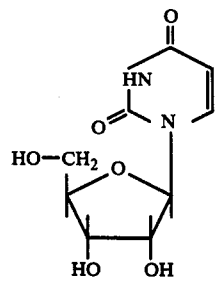

into the corresponding $R_1'$ substituted compound III below, by reacting the derived $O^2$,2'-cyclouridine with an alkali azide (when $R_1'$ is azide) or with a halide (when $R_1'$, is halogen) or the uridine with an alkylation agent (when $R_1'$ is alkoxy)

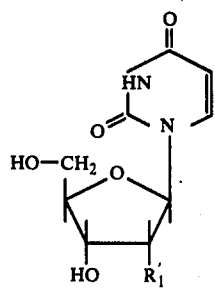

wherein $R_1'$ is azide, halogen, or alkoxy;

(b) transforming Compound III with hydrazine into a 2-deoxy-ribose compound of the formula IV

(c) converting the 2-deoxy-ribose compound IV with methanol in the presence of a strong acid into a 1-O-methylglucoside of the formula V

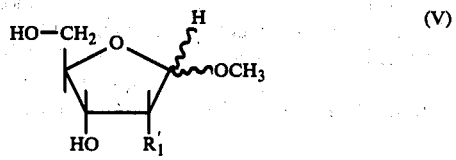

(d) reacting the glucoside V with acetic anhydride, in a polar organic solvent, to form a 1-O-methyl-ribose-3,5-diacetate of formula VI

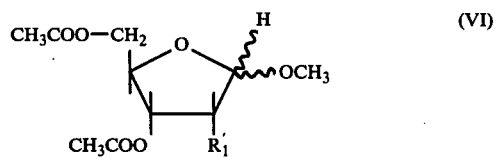

(e) converting the diacetate VI with acetic anhydride in glacial acetic acid, in the presence of a strong acid into a ribose-1,3,5-triacetate of formula VII

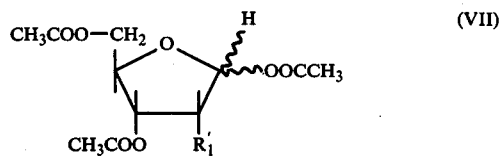

(f) condensing the obtained triacetate with a purine base wherein the free primary amino group is protected by acylation, in an organic solvent in the presence of Lewis acid and converting the product obtained to split the acyl group yielding a compound of formula I in which $R_1$ is azide, halogen, or alkoxy;

(g) optionally separating the product obtained into its α and β anomers; and (h) optionally reacting Compound I in which $R_1$ is azido with triphenylphosphine in saturated methanolic ammonia, into the corresponding Compound I where $R_1$ is amino;

wherein $R_1'$ in formulas IV, V, VI and VII is defined as in formula III above.

2. Process as claimed in claim 1 wherein in step (a) Compound II is reacted with an alkali azide by first reacting the uridine Compound II with diphenylcarbonate in hexamethylphosphoric acid triamide at a temperature of about 140° C., in the presence of a little sodium bicarbonate and reacting same with lithium azide at an elevated temperature.

3. Process as claimed in claim 1 wherein in step (b) Compound III is treated with an aqueous hydrazine hydrate solution at a temperature of about 40° to 80° C.

and reacting the boiled down reaction product which is taken up with water, with benzaldehyde at an elevated temperature.

4. Process as claimed in claim 1 wherein in step (c) concentrated sulfuric acid is utilized as said strong acid and the reaction at a temperature of from 0° to 10° C.

5. Process as claimed in claim 1 wherein in step (f) the protected purine base is selected from $N^6$-octanoyladenine or $N^2$-palmitoylguanine, the organic solvent is 1,2-dichlorethane, the Lewis acid is stannic tetrachloride and the acyl groups are split with sodium methylate in methanol.

6. Process as claimed in claim 1 wherein in step (a) Compound II is reacted with an alkylating agent selected from diazomethane, diazoethane or benzyl halide to yield a Compound III wherein $R_1'$ is alkoxy.

7. Process as claimed in claim 1 wherein in step (a) the uridine Compound II is reacted with a halide to yield the corresponding Compound III wherein $R_1'$ is halogen.

8. Process as claimed in claim 1 wherein in step (d) said polar organic solvent is pyridine.

9. Process as claimed in claim 1 wherein step (g) is included to separate the product obtained into its $\alpha$ and $\beta$ anomers.

10. Process as claimed in claim 1 wherein step (h) is included to result in the desired compound wherein $R_1$ is amino.

11. Process as claimed in claim 1 wherein in step (b) Compound III is mixed in aqueous hydrazine hydrate solution at a temperature from 40° to 80° C., the evaporated reaction product recombined with water treated with benzaldehyde and heated in a bath of boiling water while being mixed.

* * * * *